(12) United States Patent
Lendi

(10) Patent No.: US 9,588,090 B2
(45) Date of Patent: Mar. 7, 2017

(54) METHOD FOR THE DETERMINATION OF FILM-FORMING AMINES

(71) Applicant: SWAN ANALYTISCHE INSTRUMENTE AG, Hinwil (CH)

(72) Inventor: Marco Lendi, Zürich (CH)

(73) Assignee: SWAN ANALYTISCHE INSTRUMENTE AG, Hinwil (CH)

( * ) Notice: Subject to any disclaimer, the term of this patent is extended or adjusted under 35 U.S.C. 154(b) by 0 days.

(21) Appl. No.: 14/782,632

(22) PCT Filed: Apr. 11, 2013

(86) PCT No.: PCT/EP2013/057624
§ 371 (c)(1),
(2) Date: Oct. 6, 2015

(87) PCT Pub. No.: WO2014/166542
PCT Pub. Date: Oct. 16, 2014

(65) Prior Publication Data
US 2016/0091469 A1 Mar. 31, 2016

(51) Int. Cl.
*G01N 31/22* (2006.01)
*G01N 21/25* (2006.01)
*G01N 21/78* (2006.01)
*G01N 21/77* (2006.01)

(52) U.S. Cl.
CPC ........... *G01N 31/22* (2013.01); *G01N 21/253* (2013.01); *G01N 21/78* (2013.01); *G01N 2021/7763* (2013.01); *G01N 2021/7769* (2013.01); *G01N 2201/0621* (2013.01)

(58) Field of Classification Search
CPC ...................................... G01N 31/22
USPC ............................................................ 436/85
See application file for complete search history.

(56) References Cited

U.S. PATENT DOCUMENTS 6,555,170 B2 * 4/2003 Taylor ..................... C25D 3/02
 205/125
2007/0218562 A1 9/2007 Li

FOREIGN PATENT DOCUMENTS

| EP | 0562210 A1 | 2/1993 | |
| EP | 0562210 A1 * | 9/1993 | ............. G01N 21/78 |
| SU | 828842 A1 | 4/1982 | |
| WO | 99/04256 A1 | 1/1999 | |
| WO | 2012042185 A3 | 4/2012 | |

OTHER PUBLICATIONS

Batistela et al. "pKa determinations of xanthene derivates in aqueous solutions by multivariate analysis applied to UV—Vis spectrophotometric data" Spectrochimica Acta Part A 79 (2011) 889-897.*
International Preliminary Report on Patentability for PCT/EP2013/057624 filed Apr. 11, 2013.
(Continued)

*Primary Examiner* — Christine T Mui
*Assistant Examiner* — Emily Berkeley
(74) *Attorney, Agent, or Firm* — Notaro, Michalos & Zaccaria P.C.

(57) ABSTRACT

Within a method for the determination of film-forming amines in liquids by adding a reacting agent with the amine to form a colored complex to be measured by photometric method for the reaction the pH of the liquid mixture is lowered by using hydrochloric acid.

10 Claims, 2 Drawing Sheets

(56) References Cited

OTHER PUBLICATIONS

Figure 1:
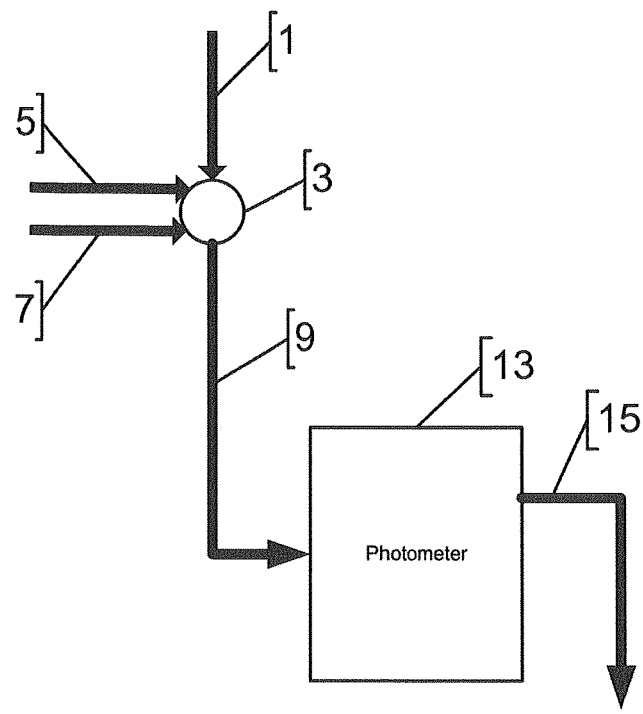

International Search Report for PCT/EP2013/057624 filed Apr. 11, 2013.
Written Opinion for PCT/EP2013/057624 filed Apr. 11, 2013.
Albert. Millin et al, "Determination of Traces of Fatty Amines in Water", Analytical Chemistry, vol. 28, No. 7, Jul. 1, 1956.
Silverstein RM: "Spectrophotometric Determination of Primary, Secondary, Andtertiary Fatty Amines in Aqueoussolution", Analytical Chemistry, American Chemical Society, US, vol . 35, No. 2, Feb. 1963, p. 154-157.
D'Amboise M et al: "Trace determination of gaseous chlorine: a comparison between an electrometric method and the methyl orange photometric method", Analytica Chimica Acta, Elsevier, Amsterdam, NL, vol. 104, No. 2, Feb. 1979, pp. 355-361.
Yu. M. Evtushenko et al., "Photometric determination of Octadecylamine with methyl orange", Journal of Analystical Chemistry, vol. 57, No. 1, p. 8-11 (Dec. 31, 2002).
Stiller, Karen, et al., "The Analysis of Film-Forming Amines—Methods, Possibilities, Limits and Recommendations", PowerPlant Chemistry 2011, 13(10), Waesseri GmbH, pp. 602-611.

* cited by examiner

METHOD FOR THE DETERMINATION OF FILM-FORMING AMINES

The present invention refers to a method for the determination of film-forming amines in liquids by adding a reacting agent to the amine to form a colored complex to be measured by photometric method and in particular to the determination of the concentration of amines in solutions used for the inside coating of pipelines, tubes, reactors and the like, to prevent corrosion, in particular in water-steam cycles of power plants.

At present feed-water additives based on film-forming amines are used to the inside treatment or coating respectively of pipelines, tubes, reactors and the like in industrial plants to prevent those items against corrosion. Film-forming amines, such as often known as polyamines or fatty amines, are characterized with the general formula $$R^1-(NH-R^2-)_n-NH_2$$

where n: stands for a natural number or integer between 0 and 7,
$R^1$: for non-branched alkyl chains with 12 to 18 C-atoms, and
$R^2$: for short chained alkyl groups with 1 to 4 C-atoms.

The amines are used as additives e.g. in water-steam cycles, suitable as corrosion inhibiters, forming very thin films on the inside surface of e.g. pipelines, tubes, reaction vessel and the like of e.g. an industrial power plant.

Like classical treatment concepts, treatments with film-forming amines are critical in relation to their concentration in the liquid, which means, the concentration has to be measured carefully to ensure a successful treatment or coating respectively, to avoid unnecessary overdosing of the polyamines and corresponding adverse effects such as clogging of filters.

Various concepts are known for determining the concentration of polyamines in liquids as e.g. mentioned in feed-water or water-steam cycles in power plants. E.g. the EP 0 562 210 is proposing a method for the simple and sensitive determination of polyamines in liquids, and a photometer for performing this method. A color formation of the polyamines in a sample is determined by a nearly monochromatic light coming from a conventional LED and filtered by a colored glass filter. The color forming reaction in the method of the invention is based on the reaction of polyamines to be assayed with sodium 3,4,5,6-tetrachloro-2',4',5',7' tetraiodofluorescein, commonly known as Bengal-rosa B.A., where the reaction is executed in a pH-buffered solution using acetic acid.

A similar method is described within the Article by Yu. M. Evtushenko, V. M. Ivanov, and B. E. Zaitsev "Photometric Determination of Octadecylamine with Methyl Orange", Journal of Analytical Chemistry, Vol. 57, No. 1, 2002, pp. 8-11, where the reaction of the amine with Methyl Orange in water at a pH value of 2.5 to 4 was studied.

Within the Article by Katrin Stiller, Tobias Wittig and Michael Urschey "The Analysis of Film-Forming Amines—Methods, Possibilities, Limits and Recommendations", PowerPlant Chemistry 2011, 13(10), describes treatment concepts of water-steam cycles based on film-forming amines. Again, the studies are based on the use of the above mentioned Bengal rose method. Within this Article it has been pointed out that treatment with film-forming amines must be carefully monitored in order to ensure successful treatment and a high degree of operational safety. The studies within this Article are based on the treatment of the amine with Bengal rose with the pH of the samples being between 2.3 and 3.3. It has been shown that the method is very pH sensitive and that after the reagent addition, which means of the Bengal rose addition, the pH of the sample must be absolutely between 2.3 and 3.3 to ensure reliable results of the concentration measurement of the amines.

The practice has shown that all the proposed methods are quite time consuming as, first of all, it is of great importance to buffer the solution as mentioned within the range of 2.3 to 3.3 and furthermore the reaction is quite slow. Therefore, concentration measurements so far can only be executed batch-vise and e.g. an online measurement is critical.

Therefore, it is an object of the present invention to propose an easy determination of the concentration of film-forming amines in solutions, which can be executed in a rather short time limit, especially compared with the actually known methods.

It is a further object of the present invention to determine the concentration of film-forming amines used in feed-water or water-steam cycles in power plants used as corrosion inhibiters by coatings of pipelines, tubes, reactors and the like of industrial power plants.

Again, a further object of the present invention is to propose a method as mentioned above, to enable online measurement of the concentration of film-forming amines.

According to the present invention, a method is proposed for the determination of film-forming amines in liquids by adding a reacting agent having a $pK_a$ value to the amine to form a colored complex to be measured by photometric method, characterized in that for the reaction hydrochloric acid is used.

According to the present invention it is proposed to determine the presence and concentration of the film-forming amines by reacting with a reacting agent enabling the formation of a colored complex and by further adding a solution containing hydrochloric acid.

According to a further aspect it is proposed to add hydrochloric acid to lower the pH value of the reacting solution of the reacting agent with the film-forming amine to a value lower to the $pK_a$ value of the reacting agent provided for forming the colored complex.

It is further proposed to lower the pH value to a pH of ≤2.3, preferably ≤2.0 by adding hydrochloric acid.

Accordingly a fast and adequate lowering of the pH value is achieved.

According to a further aspect, it is proposed that as a reacting agent, a color component out of the Xanthene-Group according to the following general formula is used:

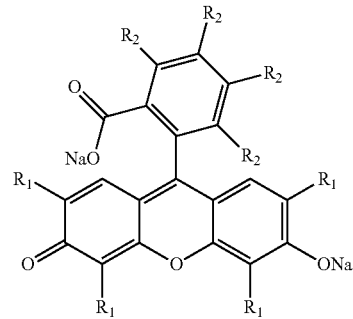

wherein $R^1$=H or a halogen, and
$R^2$=H or a halogen.

As already mentioned above, the film-forming amines to be determined are characterized according to the following general formula:

$$R^1-(NH-R^2-)_n-NH_2$$

where n stands for a natural number or integer between 0 and 7, $R^1$: for non-branched alkyl chains with 12 to 18 C-Atoms, and $R^2$: for short chained alkyl groups with 1 to 4 C-Atoms.

As reacting agent proposed are e.g. the following:

Fluorescein, Bengal rose, Eosin, Erythrosine, where the use of Eosin is preferred.

The great advantage of the method according to the present invention is that direct photometric determination of the colored complexes in aqueous solution is possible. E.g. as also proposed in the prior art, no phase transfer into an organic solvent is necessary, as e.g. described within the Literature BS2690, part 117:1983 with the title: "Long-chain fatty amines : spectrophotometric method".

The method as proposed according to the present invention does not show any selectivity against any other components which might be present within the liquid solution, such as the feed-water, like e.g. Ammonia, Cyclohexylamine, Ethanolamine, Morpholine, and the like.

Nevertheless, there are also some disadvantages by having a too low pH value, as the reaction time of the reacting agent at the level of its $pK_a$-value is very fast, while the lower the pH value is, the slower is the reaction. In other words, a pH value of 1.5 or lower is not preferred.

The discolored reacting agent, which means the dye stuff at low pH-value is not anymore soluble in water and does precipitate.

The method as proposed according to the present invention can be executed either in a so called batch-vise method or, which is preferred, as using so-called direct flow injection.

Figure 2:
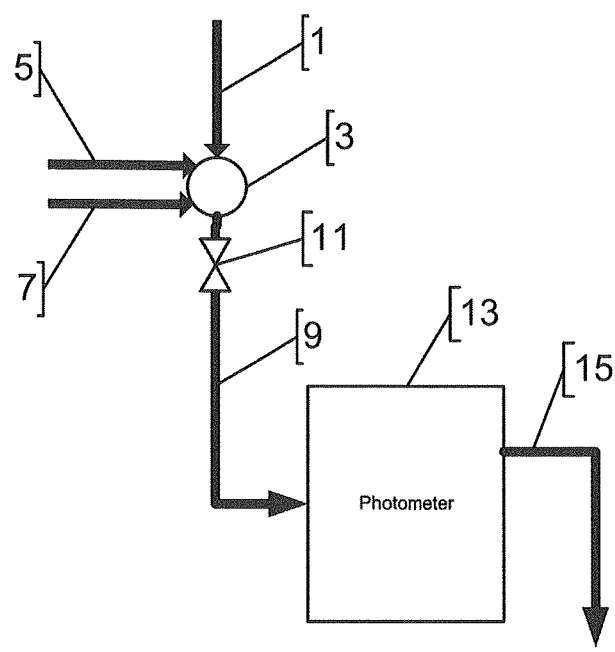
Figure 3:
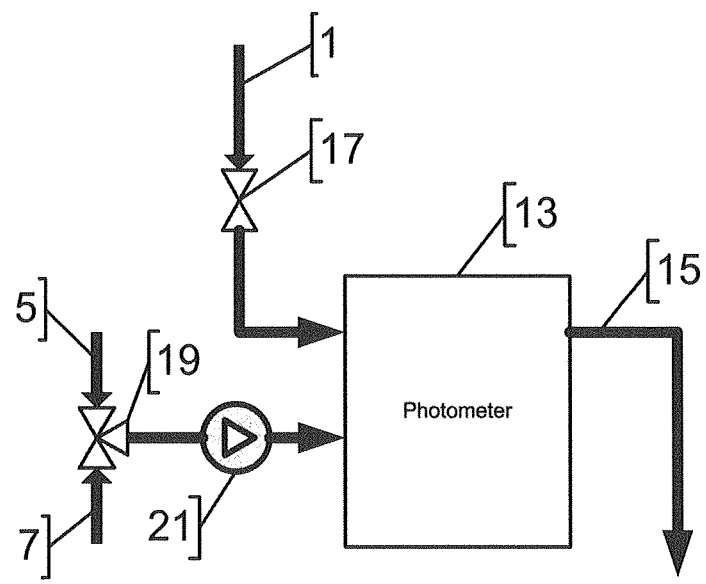

With reference to the attached figures, three examples of the execution of the method according to the present invention are described:

FIG. 1 shows a direct flow injection method, where no interruption of the inlet probe takes place when mixing with reacting agents and following measurement in the photometric device, FIG. 2 shows a similar test arrangement as FIG. 1, but with interruption of the inlet probe when mixing with reacting agents, and FIG. 3 shows the measuring method, where the mixing procedure of the liquid solution containing the film-forming amine with the reacting agents takes place within the photometric device.

FIG. 1 shows a first embodiment of the inventive method in the sense of a principal representation. Through a first line 1, the inlet of a probe of the feed-water or water-steam cycle containing the film-forming amine is introduced into a mixing chamber 3. The first reacting agent, which is a Xanthene dye stuff diluted in water, is added via inlet 5 into the mixing chamber, at the same time with the second reacting agent via inlet 7, which is a hydrochloric acid solution to lower the pH value to the total solution to a value of lower of the $pK_a$ value of the Xanthene dye stuff.

The adding of the two reacting agents is carried out at the same time with e.g. an adding velocity of approx. 3.5 ml/min during 10 sec. Afterwards the reacting mixture is flowing through a conduit or connecting passage 9, which can be e.g. a so-called reacting spiral to the photometric measuring device 13, where the measuring is executed. The reaction mixture requires only a few seconds to flow from the mixing chamber to the photometric measuring device. The measuring is executed with a wave-length in a range between 400 and 560 nm dependent upon the Xanthene dye stuff being used.

Within the following Table 1 various possible Xanthene dye stuff reacting agents are listed in the sense of examples, which can be used to determine the concentration of film-forming amines. In Table 1 also the wave-length is indicated, at which the photometric detection is made in dependence of the used dye stuff as reacting agent. The great advantage of the present invention is that the photometric detection can be made in a simple photometric measuring device using an ordinary LED source.

| Name | $R_1$ | $R_2$ | $\lambda_{max}$ [nm] |
|---|---|---|---|
| Bengal Rose | I | Cl | 570 |
| Eosin | Br | H | 540 |
| Erythrosin | I | H | 500 |

FIG. 2 shows a second embodiment of the inventive method, again in the sense of a principal representation. In principle, a similar method as described with reference to FIG. 1 is executed with the difference that after the mixture is introduced via the conduit 9 into the photometric measuring cell, valve 11 is closed. So the reacting mixture remains within the photometric measuring device 13. After a certain reaction time, which is dependent upon the doses of the reacting agents and furthermore from the pH values as well as from the temperature, again the measuring is executed within the photometric measuring device 13.

After measuring the concentration of the film-forming amine, the valve 11 is opened again and the aqueous feed-water can circulate.

In FIG. 3 a method according to a batch measurement is shown, where the mixing between the various reacting agents with the feed-water takes place within the photometric device 13 itself. The inlet of the feed-water or water steam cycle 1 is introduced into the photometric device. Before starting the measuring process the inlet flow is interrupted by the valve 17. As a result the test sample of the water cycle remains stationary within the photometric device. First the first reacting agent, which means the Xanthene dye stuff, is pumped via inlet 5 using a pump 21 into the photometric device 13. After adding the first reacting agent the valve 19 switches to the second reacting agent, which is hydrochloric acid. Again the adding is effected via inlet 7 by using the pump 21. After the addition of the two reacting agents a reacting time of approx. 13 sec takes place. Afterwards the measuring is executed and finally valve 17 again is opened and the test solution is removed via the outlet 15.

Example 1:

Using the embodiment as shown in FIG. 1, the following practical example has been executed:

Flow rate with the first inlet line: 80-90 ml/min

Temperature of the inlet flow: 20-35° C.

pH-value of the inlet flow varies between 7.5 and 10.5 (mixture of feed-water, film-forming amine and Ammonia, Ethanolamine and Morpholine as alkalinizing additives)

As first reacting agent: 1.4 g Eosin disodium salt (purity >85%) diluted in 2000 g totally desalinated water combined with 3 g of a wetting agent (non-ionic tenside).

Second reacting agent: Recipe for the production of a 2 l buffering solution: 1270 ml of 2.5 M Glycin mixed with 730 ml 2.5 M HCl.

Sequence of the measuring process:

Minimal measuring interval: 1 min.

Measuring range: 0.05 ppm-5 ppm

Example 2:

Using the embodiment as shown in FIG. 2 the following practical example has been executed:

Flow rate of the first inlet line 1: 80-90 ml/min.

Temperature of inlet flow: 20-35° C.

pH value of inlet flow between 7.5 and 10.5 (mixture of feed water, film-forming amine and Ammonia, Ethanolamine and Morpholine as alkalinizing additives)

Reacting time (closure of valve): 7 min.

First Reacting Agent: 1.4 g Eosin disodium salt (purity >85% diluted in 2000 g totally desalinated water together with 3 g of a wetting agent (non-ionic tenside)

Second reacting agent: 5 M HCl

Sequence of the measuring process:

Minimal interval of measuring: 10 min.

Measuring range: 0.3 ppm-5 ppm.

Example 3:

Using the third embodiment the following practical example has been executed:

Flow of the inlet 1: 80-90 ml/min

Temperature of inlet: 20-35° C.

pH: 7.5-10.5 (mixture additionally containing Ammonia, Ethanolamine and Morpholine as alkalization additives)

Reacting time: 30 sec after adding the first reacting agent 5

First reacting agent: 1.4 g Eosin disodium salt (purity >85%) diluted in 2000 g totally desalinated water together with 3 g of a wetting agent (non-ionic tenside)

Second reacting agent: Recipe for the production of a 2 l buffering solution: 500 ml 2.5 M KCl are mixed with 130 ml 2.5 M HCl and filled up to 2 L with totally desalinated water (HCl/KCl buffering system)

Sequence of measuring:

Minimum interval of measuring: 5 min.

Measuring range: 0.1 ppm-5 ppm

Further to the described methods, it is of course possible to add an acid resistant detergent, which prevents the forming of a deposition, e.g. within the mixing chamber.

The methods as described with reference to FIG. 1 to FIG. 3 are only examples for the better understanding of the present invention. Of course different designs of the method are possible; important is the reduction of the pH value of the mixture of the feed-water solution with the film-forming amines with the reacting agent, forming a colored complex with the amines to a $pK_a$ value of the dye stuff, preferably <2.3.

The invention claimed is:

1. Method for the determination of film-forming amines in liquids by adding a reacting agent having a $PK_a$ value to the amine to form a colored complex to be measured by photometric method, characterized by adding hydrochloric acid to lower the pH value of the liquid solution to a value <2.3 and characterized in that the reacting agent is a component of the Xanthene Group according to the following general formula:

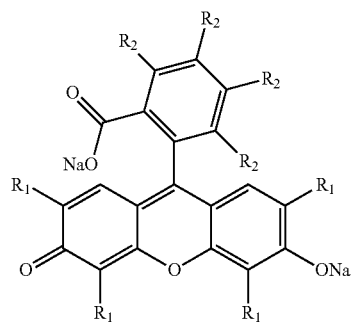

wherein, $R^1$=H or a halogen, and
$R^2$=H or a halogen.

2. Method according to claim 1, characterized in that the determination takes place in an aqueous solution having a pH value that is lower than the $pK_a$ value of the reacting agent to form the colored complex with the film-forming amine.

3. Method according to claim 1, characterized in that the film-forming amine is of the following general formula:

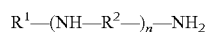

with $R^1$: non-branched alkyl chain with 12-18 C-Atoms, $R^2$: short chained alkyl chain with 1 to 4 C-Atoms, and n: natural number or integer between 0 and 7.

4. Method according to claim 1, characterized in that the reacting agent is selected from the group consisting of fluorescein, Bengal rose, Eosin and Erythrosine.

5. Method according to claim 1, characterized in that an acid resistant detergent is used to prevent the formation of a deposition.

6. Method according to claim 1, characterized in that a time in which the amine and the reacting agent react before the photometric measuring is in the range of 4 seconds to 10 minutes.

7. Method according to claim 1, characterized in that a temperature at which the amine and the reacting reagent react is in the range of 15 to 40 ° C.

8. Use of the method according to claim 1 for the determination of film-forming amines in feed-water or water steam cycles of power plants characterized in that into circular flow or a test sample containing the film-forming amine a first reacting agent is added to form a colored complex and approximately at the same time a solution containing hydrochloric acid is added, the reaction mixture is continued to a photometric measuring device or measuring cell, in which the measuring of the colored complex is executed with or without interruption of the flow.

9. Use according to claim 8, characterized in that while or after adding and mixing of the first reacting agent and the solution containing hydrochloric acid into the circular flow or the test sample the flow is interrupted and after a certain reaction time the flow of the reaction mixture is continued to the photometric measuring device, where the measuring takes place.

10. Use of the method according to claim 1 for the determination of film-forming amines in feed-water or water steam cycles of power plants characterized in that the circular flow or test sample is introduced into a photometric measuring device, the flow being interrupted, afterwards a first reacting agent containing the reacting agent forming a colored complex with the amine is added into the photometric measuring device and subsequently a second reacting agent, containing at least hydrochloric acid, is introduced into the photometric measuring device, where the reaction takes place and finally the measuring of the formed colored complex is executed.

* * * * *